United States Patent [19]

Cooper

[11] Patent Number: 5,466,843
[45] Date of Patent: Nov. 14, 1995

[54] PROCESS FOR PREPARING A $C_{12}$–$C_{24}$ SATURATED FATTY ACID ESTERIFIED ALKOXYLATED POLYOL

[75] Inventor: Charles F. Cooper, Paoli, Pa.

[73] Assignee: ARCO Chemical Technology, L.P., Greenville, Del.

[21] Appl. No.: 235,751

[22] Filed: Apr. 29, 1994

[51] Int. Cl.⁶ ............................................. C07C 51/367
[52] U.S. Cl. .................... 554/149; 554/148; 554/170; 554/171; 554/172; 554/173
[58] Field of Search .................... 554/149, 148, 554/170, 171, 172, 173

[56] References Cited

U.S. PATENT DOCUMENTS

| | | | |
|---|---|---|---|
| 4,849,242 | 7/1989 | Kershner | 426/601 |
| 4,861,613 | 8/1989 | White et al. | 426/611 |
| 4,983,329 | 1/1991 | Cooper | 260/410.7 |
| 5,059,443 | 10/1991 | Ennis et al. | 426/531 |
| 5,077,073 | 12/1991 | Ennis et al. | 426/531 |
| 5,118,448 | 6/1992 | Cooper | 554/168 |
| 5,135,683 | 8/1992 | Cooper | 554/151 |
| 5,175,323 | 12/1992 | Cooper | 554/164 |
| 5,266,346 | 11/1993 | Klemann et al. | 426/611 |
| 5,288,884 | 2/1994 | Cooper | 554/168 |
| 5,298,637 | 3/1994 | Cooper | 554/169 |
| 5,304,665 | 4/1994 | Cooper et al. | 554/149 |
| 5,308,634 | 5/1994 | Cooper | 426/531 |

FOREIGN PATENT DOCUMENTS

| | | |
|---|---|---|
| 481523 | 4/1992 | European Pat. Off. . |
| 571219 | 11/1993 | European Pat. Off. . |

*Primary Examiner*—José G. Dees
*Assistant Examiner*—Deborah D. Carr
*Attorney, Agent, or Firm*—Stephen D. Harper

[57] ABSTRACT

Esterified alkoxylated polyols containing long chain saturated linear acyl groups are obtained by esterification of an alkoxylated polyol such as propoxylated glycerin with a $C_{12}$–$C_{24}$ fatty acid such as behenic acid and recovery of excess fatty acid by treatment with an aliphatic hydrocarbon. Esterified alkoxylated polyols prepared in this manner are useful fat substitutes for the formulation of reduced calorie food products.

23 Claims, No Drawings

PROCESS FOR PREPARING A $C_{12}$–$C_{24}$ SATURATED FATTY ACID ESTERIFIED ALKOXYLATED POLYOL

FIELD OF THE INVENTION

This invention relates to methods whereby $C_{12}$–$C_{24}$ saturated fatty acid-esterified alkoxylated polyols useful as reduced calorie fat substitutes may be conveniently and economically prepared. The invention provides a process wherein excess unreacted $C_{12}$–$C_{24}$ saturated fatty acid may be readily recovered from an esterification reaction product.

BACKGROUND OF THE INVENTION

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from the fat substitutes is considerably reduced as compared to common vegetable oils, animal fats, and other lipids. The use of such substances thus enables the preparation of reduced calorie food compositions useful in the control of body weight.

U.S. Pat. No. 4,861,613 (incorporated herein by reference in its entirety) describes one class of particularly useful fat substitutes wherein a polyol such as glycerin is alkoxylated with an epoxide such as propylene oxide and then esterified with any of a number of fatty acids or fatty acid derivatives to form an esterified alkoxylated polyol. These substances have the physical and organoleptic properties of conventional triglyceride lipids, yet are significantly lower in available calories than edible oils owing to their pronounced resistance towards absorption and pancreatic lipase enzymatic hydrolysis. The thermal and oxidative stability of the esterified alkoxylated polyols renders them especially suitable for use in the preparation of reduced calorie food compositions requiring exposure to high temperatures such as fried or baked foods.

Unfortunately, as a consequence of their hydrolytic stability and low digestibility, fully liquid versions of esterified alkoxylated polyols described in U.S. Pat. No. 4,861,613 may tend to cause certain undesirable gastrointestinal side effects when consumed at high levels in the diet. That is, since such esterified alkoxylated polyols are not readily broken down into simpler substances upon ingestion, they largely retain their oily, fat-like character and pass through the digestive tract in substantially unaltered form. Non-digestible fat substitutes in general often function as laxatives in much the same manner as mineral oil. Problems with diarrhea, leakage of the fat substitute through the anal sphincter, separation of the fat substitute as an oil from the excreted fecal matter, and shortened bowel transition times resulting in gastrointestinal discomfort can occur as a result of the non-digestibility of the fat substitutes. Other fat substitutes which are similarly resistant towards digestion are also known to produce such gastrointestinal side effects. Examples include sucrose polyester which is esterified with up to 8 fatty acid groups; see U.S. Pat. Nos. 3,954,976, 4,005,195, 4,005,196, and 5,006,360. Obviously, such problems will greatly limit the maximum usage level of these substances which can be tolerated in various food compositions, thereby constraining the amount of conventional triglyceride and the number of calories which can be removed from certain foods.

One solution to this problem is provided in European Patent Publication No. 571,219. This European application describes a fatty acid-esterified propoxylated glycerin composition useful as a reduced calorie fat substitute resistant to gastrointestinal side effects having an average number of oxypropylene units per equivalent of glycerin of from 3 to 20, a fatty acid acyl group content such that at least 40 mole percent of the fatty acid acyl groups in the composition are derived from a $C_{20}$–$C_{24}$ saturated linear fatty acid, and a solid fat index at 27° C. as measured by dilatometry of at least 30. The utilization of such a composition in combination with a conventional fully digestible fatty acid triglyceride fat or oil in a food composition normally containing a fatty component is also described. The European application suggests that these fatty acid-esterified propoxylated glycerin compositions may be obtained by first propoxylating glycerin with the desired number of equivalents of propylene oxide and then esterifying with a fatty acid or fatty acid equivalent such as a fatty acid ester, or fatty acid halide, or a fatty acid anhydride.

The use of fatty acid esters in such an esterification step is described in U.S. Pat. No. 5,175,323 (incorporated herein by reference in its entirety). The fatty acid esters employed in this process are $C_1$–$C_4$ alkyl esters of saturated or unsaturated $C_{10}$–$C_{24}$ fatty acids. The esterification reaction is readily driven to completion by removing the $C_1$–$C_4$ aliphatic alcohol generated during the transesterification reaction by distillation or similar means. Although this approach works well on a laboratory scale and affords a high yield of esterified alkoxylated polyol with minimal by-products or color formation, it suffers from the practical disadvantage that the required $C_1$ to $C_4$ alkyl esters are relatively expensive as compared to the corresponding free fatty acids. In addition, great care must be taken to ensure that all of the residual $C_1$–$C_4$ aliphatic alcohol formed is removed from the product prior to use in a food composition since certain alcohols of this type (methanol, for example) are considered harmful when ingested.

However, if the $C_{20}$–$C_{24}$ saturated linear acyl groups in the esterified propoxylated glycerin compositions of European Patent Publication No. 571,219 are introduced using the corresponding free fatty acids rather than the $C_1$–$C_4$ alkyl esters in order to reduce the overall cost of the esterification, certain other processing problems are encountered. In particular, unless an acidic catalyst such as a sulfonic acid is used (which may be difficult to remove quantitatively when esterification is completed), a fairly large excess (10–30% molar excess) of fatty acid relative to the initial hydroxyl concentration must be utilized in order to self-catalyze the reaction and to accomplish complete or near-complete esterification of the propoxylated glycerin. As a consequence, the excess fatty acid which remains at the completion of the esterification must be removed prior to formulation of the fat substitute into a food composition; excess fatty acid may cause severe taste, odor, and stability problems. One possible way to remove the excess fatty acid is by vacuum steam stripping the acids away from the esterified propoxylated glycerin composition. This procedure is quite difficult to accomplish when $C_{20}$–$C_{24}$ saturated linear fatty acids are being employed since such acids are relatively high melting (typically, over 74° C.) and consequently readily form troublesome plugs in commercial processing equipment. At times, particularly in vacuum equipment, even steam tracing is not an effective solution due to temperature-lowering effects in the vacuum eductor. As a result, it is often nearly impossible to carry out purification of a $C_{20}$–$C_{24}$ saturated fatty acid-esterified propoxylated glycerin without having to frequently shut down to remove plugs of unreacted fatty acid. If a transition metal esterification catalyst such as a zinc, titanium, or tin compound is utilized so as to permit the use of a stoichiometric amount of fatty acid relative to propoxylated glycerin, quantitative removal of the metal catalyst following esterification is often quite difficult to achieve. To be useable as a reduced calorie fat substitute in food compositions, however, the esterified alkoxylated polyol must be essentially free of such metallic impurities.

It is therefore evident that a great need exists for improved methods of synthesizing $C_{20}$–$C_{24}$ saturated linear fatty acid-esterified propoxylated glycerin compositions.

SUMMARY OF THE INVENTION

This invention furnishes a process for preparing a $C_{12}$–$C_{24}$ saturated fatty acid-esterified alkoxylated polyol comprising the steps of (a) reacting an alkoxylated polyol with a fatty acid source comprised of a $C_{12}$–$C_{24}$ saturated fatty acid to form a crude reaction product comprised of unreacted $C_{12}$–$C_{24}$ saturated fatty acid and the $C_{12}$–$C_{24}$ saturated fatty acid-esterified alkoxylated polyol; (b) combining the crude reaction product with an aliphatic hydrocarbon; (c) precipitating the unreacted $C_{12}$–$C_{24}$ saturated fatty acid to form a biphasic mixture comprised of the precipitated $C_{12}$–$C_{24}$ saturated fatty acid and a liquid phase comprised of the aliphatic hydrocarbon and the $C_{12}$–$C_{24}$ saturated fatty acid-esterified alkoxylated polyol; (d) separating the precipitated $C_{20}$–$C_{24}$ saturated fatty acid from the liquid phase; and (e) separating the aliphatic hydrocarbon in the liquid phase from the $C_{20}$–$C_{24}$ saturated fatty acid-esterified alkoxylated polyol.

In a preferred embodiment, the invention provides a process for preparing a behenic acid-esterified alkoxylated polyol comprising the steps of (a) reacting an alkoxylated polyol obtained by reacting a polyol having n hydroxyl groups, wherein n is an integer of 2 to 8, with from n to 10 times n moles of a $C_2$–$C_6$ aliphatic epoxide with a fatty acid source comprised of behenic acid at a temperature of 150° C. to 300° C. to form a crude reaction product comprised of unreacted behenic acid and the behenic acid-esterified alkoxylated polyol; (b) combining the crude reaction product with a $C_5$–$C_9$ aliphatic hydrocarbon, wherein the weight ratio of crude reaction product: aliphatic hydrocarbon is from 1:0.5 to 1:10; (c) precipitating the unreacted behenic acid to form a biphasic mixture comprised of the precipitated behenic acid and a liquid phase comprised of the $C_5$–$C_9$ aliphatic hydrocarbon and the behenic acid-esterified alkoxylated polyol; (d) separating the precipitated behenic acid from the liquid phase by filtration; and (e) separating the $C_5$–$C_9$ aliphatic hydrocarbon in the liquid phase from the behenic acid-esterified alkoxylated polyol by distillation.

DETAILED DESCRIPTION OF THE INVENTION

In one step of the process of the invention, an alkoxylated polyol is reacted with a fatty acid source comprised of a $C_{12}$–$C_{24}$ saturated fatty acid to form a crude reaction product comprised of unreacted $C_{12}$–$C_{24}$ saturated fatty acid and the desired $C_{12}$–$C_{24}$ saturated fatty acid-esterified alkoxylated polyol. Suitable alkoxylated polyols are well-known in the art and may be obtained by any appropriate method including, for example, the alkoxylation of a polyol with one or more equivalents of an epoxide using a basic, acidic, or coordination catalyst.

The polyol may be any organic compound bearing two or more hydroxyl groups and preferably is aliphatic in character; nitrogenous, aromatic, and halide groups are preferably not present in the polyol. The polyol may be selected from $C_2$–$C_{10}$ aliphatic diols (e.g., ethylene glycol, propylene glycol, 1,3-propanediol, 1,4-butanediol, 1,2-butanediol, 2,3-butanediol, pinacol, 1,2-cyclohexanediol, 1,2-pentanediol, 1,4-pentanediol, 1,5-pentanediol, 2,4-pentanediol, 3,3-dimethyl-1,2-butanediol, 2-ethyl-2-methyl-1,2-propanediol, 1,2-hexanediol, 1,5-hexanediol, 1,6-hexanediol, 2,5-hexanediol, 2-methyl-2,4-pentanediol, 1,4-cyclohexanediol, 1,7-heptanediol, 2-methyl-2-propyl-1,3-propanediol, 2,2-diethyl-1,3-hexandiol, 1,2-octanediol, 1,8-octanediol, 2,2,4-trimethyl-1,2-pentanediol, and the like), $C_3$–$C_{12}$ aliphatic triols (e.g., glycerin, 1,2,4-butanetriol, 2,3,4-pentanetriol, 2-ethyl-2-(hydroxymethyl)- 1,3-propanediol, 1,1,1-tris(hydroxymethyl)ethane, 1,2,6-trihydroxyhexane, 1,2,3-heptanetriol, and the like), $C_4$–$C_{12}$ aliphatic tetrols (e.g., sorbitan, erythritol, pentaerythritol), $C_5$–$C_8$ sugar alcohols [including those compounds corresponding to the formula $HOCH_2(CHOH)_n CH_2OH$ wherein n is 3 to 6 such as xylitol, sorbitol, arabitol, mannitol, and the like], monosaccharides (e.g., erythose, threose, ribose, arabinose, xylose, lyxose, allose, altrose, glucose, mannose, gulose, idose, galactose, fructose, talose, and the like), disaccharides (e.g., sucrose, maltose, lactose) and alkyl glycosides (e.g., methyl glycosides, ethyl glycosides, propyl glycosides, and other glycoside molecules wherein the alkyl glycoside is an acetal formed by interaction of a $C_1$–$C_{20}$ alcohol with a carbonyl group of a mono- or disaccharide such as glucose). Most preferably the polyol is glycerin (also known as glycerol).

The epoxide may be any organic compound containing a three-membered cyclic ether (oxirane) group. Preferred epoxides include $C_2$–$C_{10}$ epoxides, especially $C_2$–$C_6$ aliphatic epoxides, such as ethylene oxide, propylene oxide, 1,2-butylene oxide, (cis and/or trans) 2,3-butylene oxides, isobutylene oxide, 1,2-pentene oxide, cyclohexene oxide, phenyl glycidyl ether, methyl glycidyl ether, ethyl glycidyl ether, styrene oxide, epichlorohydrin, allyl glycidyl ether, and the like. Due to their low cost, high reactivity, and favorable impact on esterified alkoxylated polyol fat substitute properties, the use of ethylene oxide, propylene oxide, 1,2-butylene oxide or mixtures thereof (either in random or block fashion) is especially desirable.

Typically, from n to 10 n equivalents of the epoxide are reacted with the polyol wherein n corresponds to the number of hydroxyl groups on the polyol and is preferably from 2 to 8. In preferred embodiments, the alkoxylated polyol has the general structure $R-[-O-(oxyalkylene)_x-H]_n$ wherein R is an organic moiety derived from the polyol, oxyalkylene is a ring-opened epoxide unit, x is an integer of from 1 to 10, and n is an integer of 2 to 8. Oxyalkylene is most preferably oxyethylene, oxypropylene, oxybutylene, or some combination thereof and thus may correspond to the general structure

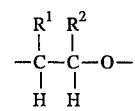

wherein $R^1$ and $R^2$ are the same or different and are hydrogen or an alkyl group such as methyl or ethyl. In one desirable embodiment, $R^2$ in the terminal oxyalkylene group is an alkyl group since a secondary ester linkage highly resistant to enzymatic hydrolysis will thereby be created in the $C_{12}$–$C_{24}$ saturated fatty acid-esterified alkoxylated polyol product.

The fatty acid source to be reacted with the alkoxylated polyol is comprised of at least one $C_{12}$–$C_{24}$ saturated linear fatty acid, but may be additionally comprised of other fatty acids such as branched, unsaturated, and/or lower carbon number (e.g., $C_6$–$C_{11}$) fatty acids. Suitable $C_{12}$–$C_{24}$ saturated linear fatty acids include, for example, lauric acid, myristic acid, palmitic acid, stearic acid, eicosanoic (arachidic) acid, docosanoic (behenic) acid, and tetracosanic (lignoceric) acid. Mixtures of $C_{12}$–$C_{24}$ saturated linear fatty acids may advantageously be employed. Such fatty acids may be synthetically prepared using known methods or obtained from natural sources such as triglycerides. For example, natural oils or fats containing $C_{20}$–$C_{24}$ unsaturated ester groups may be converted to saturated form by hydrogenation either before or after hydrolysis. Lipids containing significant quantities of $C_{20}$–$C_{24}$ ester groups include, for example, high erucic rapeseed oil, meadowfoam oil, mustard seed oil, wallflower oil, fanweed oil, nasturtium seed oil, Crambe oils and the like. Preferably, at least 20 mole percent (more preferably at least 40 mole percent) of the fatty acids reacted with the alkoxylated polyol are $C_{12}$–$C_{24}$ (more preferably, $C_{20}$–$C_{24}$) saturated linear fatty acids, although up to 100% of the fatty acids reacted may be of this type if so desired. The balance of the fatty acids comprising the fatty acid source may be any of the other known saturated linear fatty acids falling outside the $C_{12}$–$C_{24}$ range or having unsaturated and/or branched structures including, for example, caproic acid, caprylic acid, pelargonic acid, capric acid, undecyclic acid, myristoleic acid, palmitoleic acid, oleic acid, elaidic acid, vaccenic acid, gadoleic acid, cetoleic acid, erucic acid, linoleic acid, linolenic acid, and the like and mixtures thereof. Although the process of this invention may be carried out using the fatty acid(s) and the alkoxylated polyol in any proportion, it will generally be desirable where the $C_{12}$–$C_{24}$ saturated fatty acid esterified alkoxylated polyol is to be utilized as a fat substitute to accomplish substantially complete esterification of the alkoxylated polyol. That is, at least 67% and more preferably at least 90% of the hydroxyl groups of the alkoxylated polyol are preferably transformed into ester groups. Typically, a 5 to 40% stoichoimetric excess of the fatty acid relative to the desired degree of esterification to be achieved is utilized. For example, if 80% esterification of one mole of a propoxylated glycerin is desired, the amount of fatty acid source employed is preferably from about 2.52 ($^{80}/_{100}\times$ $^{105}/_{100}\times 3$) to 3.36 1($^{80}/_{100}\times^{140}/_{100}\times 3$) moles.

The excess fatty acid serves to self-catalyze the esterification process, thus eliminating the need to employ additional acidic or metallic catalysts. If desired, however, any conventional esterification catalyst could be used. The esterification reaction may be readily monitored by standard means such as hydroxyl number and the reaction halted when the target degree of esterification is realized.

The temperature at which the alkoxylated polyol is reacted with the fatty acid source is not critical, but should be sufficient to accomplish the desired degree of esterification within a practically short period of time (typically, 0.5 to 18 hours) while avoiding substantial decomposition or by-product formation. The optimum temperature thus will vary greatly depending upon the reactants used and their relative proportions, among other factors, but typically temperatures in the range of from 150° C. to 300° C. (more preferably, 200° C. to 275° C.) will be effective where the esterification is being self-catalyzed by the excess fatty acid.

The esterification rate can be suitably enhanced by providing a means for removing or binding the water generated during esterification so as to drive the reaction to completion or near completion. For example, a reduced pressure of from about 0.01 mm up to atmospheric pressure (more preferably, from 1 to 50 mm) may be utilized to take the water overhead. An inert gas such as nitrogen, helium, an aliphatic hydrocarbon, carbon dioxide or the like may be sparged or passed through the reaction mixture in order to remove the water as it is formed. Azeotropic distillation of the water with a suitable azeotropic agent (entrainer) such as an aliphatic or aromatic hydrocarbon will also be effective for this purpose. The use of molecular sieves or other water absorbing or reactive substances may also be helpful in reducing the reaction time required to achieve a high degree of hydroxy group conversion. The conditions for water removal are selected such that a minimum amount of fatty acid is taken overhead.

The crude reaction product obtained by esterification of the alkoxylated polyol, which will be comprised of unreacted $C_{12}$–$C_{24}$ saturated fatty acid and the $C_{12}$–$C_{24}$ saturated fatty acid-esterified alkoxylated polyol, is combined with an aliphatic hydrocarbon. Preferably, the aliphatic hydrocarbon is nonpolar (i.e. has a low dielectric constant) and has a boiling point of from −20° C. to 175° C. at atmospheric pressure. In one embodiment, the aliphatic hydrocarbon is added to the crude reaction product when the esterification has reached the desired degree of completion. In other embodiments, however, all or a portion of the aliphatic hydrocarbon is present during the course of esterification since it may advantageously serve as a diluent, viscosity reducer, dispersant, solvent, or the like at the reaction temperatures typically utilized. The aliphatic hydrocarbon is selected such that it is relatively non-polar in character; preferably, it will contain from 5 to 9 carbon atoms and may be linear, branched or cyclic in structure. Illustrative aliphatic hydrocarbons appropriate for use include pentane, heptane, hexane, octane, nonane, cyclohexane, methyl cyclohexane, cyclopentane, cyclooctane, dimethylcyclohexane, isopentane, neopentane, 3-methyl pentane, isohexane, 2,3-dimethyl butane, neohexane, 2-ethyl hexane, and the like and mixtures thereof including commercially available mixtures such as those products sold under the names "hexanes" and "petroleum ether".

Sufficient aliphatic hydrocarbon is combined with the crude reaction product to precipitate in solid form at least a portion (preferably, at least 75%) of the unreacted $C_{12}$–$C_{24}$ saturated fatty acid to form a biphasic mixture comprised of the precipitated $C_{12}$–$C_{24}$ saturated fatty acid (in solid form) and a liquid phase comprised of the aliphatic hydrocarbon and the $C_{12}$–$C_{24}$ saturated fatty acid-esterified alkoxylated polyol. Surprisingly, it has been found that while $C_{12}$–$C_{24}$ saturated fatty acids are difficultly soluble in aliphatic hydrocarbons, $C_{12}$–$C_{24}$ saturated fatty acid-esterified alkoxylated polyols are readily soluble or miscible with such substances. The esterified alkoxylated polyol and the aliphatic hydrocarbon thus form a substantially homogeneous liquid phase which may be conveniently separated from the precipitated $C_{12}$–$C_{24}$ saturated fatty acid.

While the relative proportion of the aliphatic hydrocarbon to the crude reaction product is not critical and may be easily optimized by routine experimentation, the weight ratio of crude reaction product (exclusive of any aliphatic hydrocarbon present) to aliphatic hydrocarbon is preferably from 1:0.5 to 1:10. Too little aliphatic hydrocarbon may result in a lower than desired degree of $C_{12}$–$C_{24}$ saturated fatty acid precipitation, since the $C_{12}$–$C_{24}$ saturated fatty acid itself will generally tend to be fairly soluble in the esterified alkoxylated polyol, while the use of an excessive quantity of aliphatic hydrocarbon is disadvantageous due to the higher costs associated with removal of the excess aliphatic hydrocarbon from the liquid phase. To maximize the amount of $C_{12}$–$C_{24}$ saturated linear fatty acid precipitated, it will often be highly beneficial to reduce the temperature during the precipitation step as compared to the temperature utilized during esterification. Thus, preferably the temperature is lowered at least 100° C. (more preferably at least 150° C.). Precipitation of the $C_{12}$–$C_{24}$ saturated linear fatty acid will typically be most effectively accomplished within the temperature range of –20° C. to 75° C. The temperature should be maintained above the temperature at which the aliphatic hydrocarbon freezes and the temperature at which the esterified alkoxylated polyol begins to solidify or precipitate from solution.

The precipitated $C_{12}$–$C_{24}$ saturated linear fatty acid is separated from the liquid phase by any of the techniques known in the art for separating a solid from a liquid including, for example, decantation, centrifugation, or filtration. The use of filtration techniques wherein solid particles separated from a liquid medium by use of a porous medium is especially desirable; such methods are well known and are described, for example, in "Filtration", in *Encyclopedia of Chemical Technology*, Talcott et al., Vol. 10, pp. 284–337 (1980). The recovered $C_{12}$–$C_{24}$ saturated linear fatty acid may be washed with additional aliphatic hydrocarbon so as to free it of esterified alkoxylated polyol. The fatty acid which is recovered may be conveniently recycled for use in further esterification steps.

The liquid phase obtained as a flitrate or supernatant is fractionated by any appropriate means including distillative means (which in this context includes evaporative means) so as to remove or separate the aliphatic hydrocarbon from the fatty acid esterified alkoxylated polyol. Where distillation is utilized, for example, the $C_{12}$–$C_{24}$ saturated fatty acid-esterified alkoxylated polyol is provided as a bottoms or heavy fraction. To enhance the rate of aliphatic hydrocarbon vaporization, super-ambient temperatures (e.g., 25° C. to 300° C.) and/or subatmospheric pressures (e.g., 0.1 up to 760 mm Hg) may be utilized. Sparging or steam distillation techniques are also useful, particularly if quantitative aliphatic hydrocarbon removal from the esterified alkoxylated polyol is desired. For food applications, it will generally be desirable to reduce the level of aliphatic hydrocarbon to 100 ppm or less. A tubular coil evaporator or a film-type evaporator such as a rising film, falling film, or wiped film evaporater may also be used to advantage, particularly when the esterified alkoxylated polyol is somewhat viscous.

The $C_{12}$–$C_{24}$ saturated fatty acid-esterified alkoxylated polyol produced by the process of this invention can be additionally purified or treated so as to render it more suitable for use in food compositions using any of the techniques known in the art for refining natural vegetable or animal oils and fats. Such techniques include, but are not limited to, degumming, bleaching, filtration, deodorization, hydrogenation, dewaxing, and the like. Any remaining unreacted fatty acid may be removed by vacuum steam stripping, caustic treatment, or the like. Various additives such as stabilizers, anti-oxidants, vitamins and so forth can also be incorporated into the esterified alkoxylated polyol.

The precipitated $C_{12}$–$C_{24}$ saturated fatty acid recovered in the process of this invention may be economically re-used in subsequent esterifications if so desired. A significant advantage of the present process is that minimal (if any) purification or other treatment will be necessary to render the recovered fatty acids directly suitable for such reuse. In contrast, caustic precipitation of the unreacted fatty acids yields alkali metal salts of the fatty acids; such salts must be acidified in order to regenerate the free fatty acids needed for esterification.

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

A propoxylated glycerin containing about 8 equivalents of reacted propylene oxide per equivalent of glycerin is combined with a mixture of ca. 85% behenic acid and 15% stearic acid (ca. 20–30% stoichiometric excess based on the hydroxyl content of the propoxylated glycerin) and heated at 250° C. and 10 mm Hg pressure for 12 hours. The crude reaction product (containing 12% free fatty acids) thereby obtained is cooled, then combined with 75 parts by weight hexane per 25 parts by weight of the crude reaction mixture. The resulting product is thereafter permitted to stand at room temperature so as to form a biphasic mixture. The biphasic mixture is filtered to obtain precipitated fatty acid in solid form. After removing the hexane from the flitrate (liquid phase) by distillation, the free fatty acid content is found to be only ca. 3%. The residual acidity could be further decreased by neutralizing the flitrate with potassium hydroxide prior to filtration. After removing the hexane, heating with magnesium silicate, and refiltering, the free fatty acid content it reduced to 0.2% (2 ppm K).

COMPARATIVE EXAMPLE 2

Fully hydrogenated high erucic rapeseed oil (100 parts) containing 15% free fatty acid (ca. 40–50% behenic acid) is combined with hexane (100 parts) and the mixture stirred and heated at reflux for 1 hour. No dissolution is apparent. After cooling overnight to room temperature, the solids present are recovered by filtration. Recovery is 95%; the recovered solids contain 12–14% free fatty acid. This example demonstrates that long chain saturated fatty acids cannot be readily separated from a triglyceride containing such fatty acids in ester form using an aliphatic hydrocarbon fractionation technique.

EXAMPLE 3

This example illustrates the recovery of stearic acid ($C_{18}$ saturated fatty acid) from an esterified alkoxylated glycerin. A mixture of a stearic acid— esterified propoxylated glycerin containing about 8 equivalents of propylene oxide per equivalent of glycerin (85 parts by weight) and stearic acid (15 parts) is combined with hexane (100 parts). The resulting mixture is heated for 1 hour with agitation 40° C. The mixture is allowed to stand 15 hours at room temperature and then for an additional 15 hours at 10° C. The precipitated solids are removed by filtration and the flitrate stripped of hexane under reduced pressure. The resulting residue is expected to contain about 75 parts of the stearic and esterified propoxylated glycerin and only about 5 parts of stearic acid.

COMPARATIVE EXAMPLE 4

A mixture of 85 parts tristearin and 15 parts stearic acid was added to hexane (500 parts) and refluxed for 30 minutes. Little dissolution was apparent. After cooling, the solids were recovered by vacuum filtration. The recovered solids (97.1 parts) had a free fatty acid content of 14.4% indicating that the stearic acid was ineffectively separated from the tristearin using this technique.

I claim:

1. A process for preparing a $C_{12}$–$C_{24}$ saturated fatty acid-esterified alkoxylated polyol comprising the steps of:
   (a) reacting an alkoxylated polyol with a fatty acid source comprised of $C_{12}$–$C_{24}$ saturated fatty acid to form a crude reaction product comprised of unreacted $C_{12}$–$C_{24}$ saturated fatty acid and the $C_{20}$–$C_{24}$ saturated fatty acid-esterified alkoxylated polyol;
   (b) combining the crude reaction product with an aliphatic hydrocarbon;
   (c) precipitating the unreacted $C_{12}$–$C_{24}$ saturated fatty acid to form a biphasic mixture comprised of the precipitated $C_{12}$–$C_{24}$ saturated fatty acid and a liquid phase comprised of the aliphatic hydrocarbon and the $C_{12}$–$C_{24}$ saturated fatty acid-esterified alkoxylated polyol;
   (d) separating the precipitated $C_{12}$–$C_{24}$ saturated fatty acid from the liquid phase; and
   (e) separating the aliphatic hydrocarbon from the $C_{12}$–$C_{24}$ saturated fatty acid-esterified alkoxylated polyol.

2. The process of claim 1 wherein the aliphatic hydrocarbon contains from 5 to 9 carbon atoms.

3. The process of claim 1 wherein the separation in step (e) is accomplished by distillation.

4. The process of claim 1 wherein the aliphatic hydrocarbon has a boiling point at atmospheric pressure of from 20° C. to 175° C.

5. The process of claim 1 wherein the weight ratio of crude reaction product: aliphatic hydrocarbon is from 1:0.5 to 1:10.

6. The process of claim 1 wherein the alkoxylated polyol is obtained by reacting a polyol having n hydroxyl groups, wherein n is an integer of 2 to 8, with from n to 10 times n moles of a $C_2$–$C_6$ aliphatic epoxide.

7. The process of claim 1 wherein the fatty acid source is additionally comprised of at least one fatty acid other than a $C_{12}$–$C_{24}$ saturated fatty acid.

8. The process of claim 1 wherein the crude reaction product is comprised of from 0.01 to 1 mole of unreacted $C_{12}$–$C_{24}$ saturated fatty acid per mole of $C_{12}$–$C_{24}$ saturated fatty acid-esterified alkoxylated polyol.

9. The process of claim 1 wherein step (a) is performed at a temperature of from 150° C. to 300° C.

10. The process of claim 1 wherein step (a) is performed at subatmospheric pressure.

11. The process of claim 1 wherein the $C_{12}$–$C_{24}$ saturated fatty acid is selected from the group consisting of lauric acid, myristic acid, palmitic acid, stearic acid, arachidic acid, lignoceric acid and behenic acid.

12. The process of claim 1 wherein at least 75% of the unreacted $C_{12}$–$C_{24}$ saturated fatty acid is precipitated in step (c).

13. The process of claim 1 wherein the separation in step (d) is accomplished by a method selected from the group consisting of filtration, decantation, and centrifugation.

14. The process of claim 1 wherein a single phase liquid mixture comprised of the crude reaction product and the aliphatic hydrocarbon is formed after step (b) and before step (c).

15. The process of claim 1 wherein steps (b) and (c) are performed simultaneously.

16. The process of claim 1 wherein the $C_{12}$–$C_{24}$ saturated fatty acid is derived from hydrogenated high erucic rapeseed oil.

17. A process for preparing a behenic acid-esterified alkoxylated polyol comprising the steps of:
   (a) reacting an alkoxylated polyol obtained by reacting a polyol having n hydroxyl groups, wherein n is an integer of 2 to 8, with from n to 10 times n moles of a $C_2$–$C_6$ aliphatic epoxide with a fatty acid source comprised of at least 40 mole % behenic acid at a temperature of 150° C. to 300° C. to form a crude reaction product comprised of unreacted behenic acid and the acid-esterified alkoxylated polyol;
   (b) combining the crude reaction product with a $C_5$–$C_9$ aliphatic hydrocarbon, wherein the weight ratio of crude reaction product:aliphatic hydrocarbon is from 1:0.5 to 1:10;
   (c) precipitating the unreacted behenic acid at a temperature at least 100° C. lower than the temperature used in step (a) to form a biphasic mixture comprised of the precipitated behenic acid and a liquid phase comprised of the $C_5$–$C_9$ aliphatic hydrocarbon and the behenic acid-esterified alkoxylated polyol;
   (d) separating the precipitated behenic acid from the liquid phase by filtration; and
   (e) separating the $C_5$–$C_9$ aliphatic hydrocarbon from the behenic acid-esterified alkoxylated polyol by distillation.

18. The process of claim 17 wherein n is 3.

19. The process of claim 17 wherein the polyol is selected from the group consisting of $C_3$–$C_{12}$ aliphatic triols, $C_4$–$C_{12}$ aliphatic tetrols, $C_5$–$C_8$ sugar alcohols, monosaccharides, disaccharides, alkyl glycosides, and glycerol oligomers.

20. The process of claim 17 wherein the polyol is glycerin.

21. The process of claim 17 wherein the $C_2$–$C_6$ aliphatic epoxide is selected from the group consisting of ethylene oxide, propylene oxide, 1,2-butene oxide, or a mixture thereof.

22. The process of claim 17 wherein the polyol is glycerin and the $C_2$–$C_6$ aliphatic epoxide is propylene oxide.

23. The process of claim 17 wherein the $C_5$–$C_9$ aliphatic hydrocarbon is selected from the group consisting of pentane, hexane, heptane, octane, nonane, cyclohexane, methyl cyclohexane, cyclopentane, cyclooctane, dimethycyclohexane, isopentane, neopentane, 3-methyl pentane, isohexane, 2,3-dimethylbutane, neohexane, 2-ethyl hexane, and mixtures thereof.

* * * * *